United States Patent [19]
Andrea et al.

[11] Patent Number: 5,393,734
[45] Date of Patent: Feb. 28, 1995

[54] HERBICIDAL PYRIDINE SULFONAMIDE

[75] Inventors: Tarig A. Andrea, Hockessin; Paul H. Liang, Wilmington, both of Del.

[73] Assignee: E. I. du Pont de Nemours and Company, Wilmington, Del.

[21] Appl. No.: 108,694

[22] PCT Filed: Mar. 5, 1992

[86] PCT No.: PCT/US92/01528

§ 371 Date: Sep. 3, 1993

§ 102(e) Date: Sep. 3, 1993

[87] PCT Pub. No.: WO92/15576

PCT Pub. Date: Sep. 17, 1992

Related U.S. Application Data

[63] Continuation-in-part of Ser. No. 666,109, Mar. 7, 1991, abandoned.

[51] Int. Cl.$^6$ .................. A01N 43/54; C07D 239/46
[52] U.S. Cl. .................................... 504/215; 544/320
[58] Field of Search ................ 504/215, ; 544/320

[56] References Cited

U.S. PATENT DOCUMENTS 4,435,206 3/1984 Levitt ........................................ 71/92

FOREIGN PATENT DOCUMENTS 232067 12/1987 European Pat. Off. .
327251  9/1989 European Pat. Off. .
88/4297  6/1988 WIPO .

*Primary Examiner*—John M. Ford

[57] ABSTRACT

A pyridine sulfonylurea herbicide, composition thereof and a method for its use that results in the control of blackgrass in cereal crops and general control of all plant growth.

10 Claims, No Drawings

HERBICIDAL PYRIDINE SULFONAMIDE

CROSS-REFERENCE TO RELATED APPLICATION

This application is a continuation-in-part of U.S. patent application Ser. No. 07/666,109, filed Mar. 7, 1991, now abandoned.

BACKGROUND OF THE INVENTION

This invention relates to a certain herbicidal sulfonamide or sulfonylurea compound, an agriculturally suitable composition thereof and a method for its use as a general or selective preemergent or postemergent herbicide.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

The "sulfonylurea" herbicides are an extremely potent class of herbicices discovered within the last few years which generally consist of a sulfonylurea bridge, —$SO_2NHCONH$—, linking two aromatic or heteroaromatic rings.

WO 88/04297 discloses herbicidal pyridinesulfonylureas of the formula $$\underset{R}{\overset{W}{\underset{||}{JSO_2NHCN-A}}}$$

wherein
J is, among others,

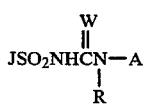

$R_1$ is $R_f$ or $R_g$;
$R_g$ is, among others, $C_1$-$C_3$ haloalkyl; and
$R_2$ is, among others, $CO_2R_9$.

Although the compound of the invention is within the above generic scope, it is not disclosed therein.

EP-A-327,251 discloses pyridinesulfonylureas of the formula

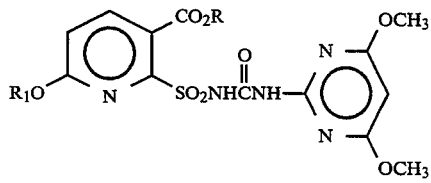

wherein
R is $C_1$-$C_3$ alkyl; and
$R_1$ is $C_1$-$C_2$ fluoralkyl and their use for controlling blackgrass.

EP-A-232,067 discloses 3-carboxamide pyridinesulfonylureas. However, this reference does not disclose the instant compound or the blackgrass utility therein.

EP-A-237,292 discloses 3-carboxamide pyridinesulfonylureas. However, this reference does not disclose the instant compound or the blackgrass utility therein.

SUMMARY OF THE INVENTION

The present invention is directed to a compound of Formula I

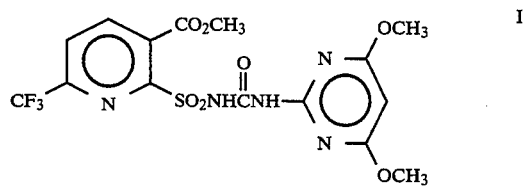

and its agriculturally suitable salts, hydrates and complexes with $C_1$-$C_4$ alcohols such as methanol, ethanol, pyranol, isopropanol and the different butyl alcohols.

The compound of the invention is highly active as a preemergent and/or postemergent herbicide for the control of blackgrass. It is especially useful for the selective control of blackgrass in cereal crops.

This invention also comprises a novel compound of Formula II which is useful as an intermediate to the compound of Formula I

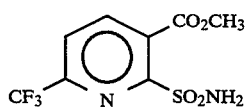

DETAILED DESCRIPTION OF THE INVENTION

Synthesis

The compound of Formula I can be synthesized by one or more of the general methods described in U.S. Pat. No. 4,774,337 and U.S. Pat. No. 4,456,469:

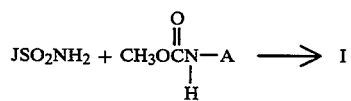

where J and A are as defined below. Alternatively, the compounds of Formula I can be synthesized by the reactions shown in Equations 1a and 1b. The reaction of sulfonamide II with the phenyl ester of the appropriate carbamic acid IIIa in the presence of various bases such as a tertiary amine base, 1,8-diazabicyclo[5.4.0]undec-7-ene (DBU) for example, is shown in Equation 1a.

The reaction of sulfonamide II with the phenyl ester of the appropriate carbamic acid IIIa in the presence of various bases such as a tertiary amine base, 1,8-diazabicyclo[5.4.0]undec-7-ene (DBU) for example, is shown in Equation 1a.

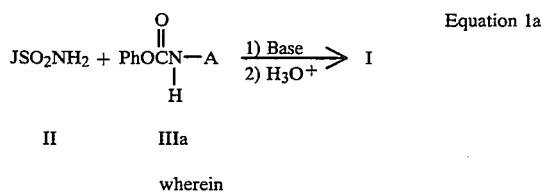

Equation 1a wherein

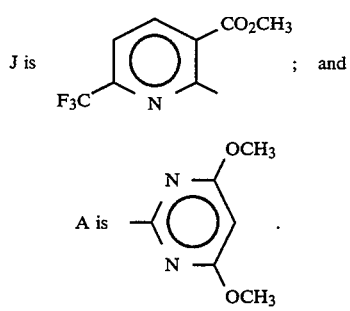

The reaction shown in Equation 1a is best carried out at 25° C. in a solvent such as, but not limited to, dioxane, tetrahydrofuran, dimethylformamide, dimethylacetamide or acetonitrile for 0.5–24 hours under an inert atmosphere as described in European Patent Application No. 70,804 (published Jan. 26, 1983). The addition of a base is advantageous. Bases especially suitable are 1,5-diazabicyclo[4,3,0]non-5-ene (DBN), 1,5-diazabicyclo[5,4,0]undec-5-ene (DBU) or triethylamine. The desired product of Formula I can be conveniently isolated by acidifying the reaction solution with aqueous hydrochloric acid. Alternatively, the aqueous layer can be extracted with a solvent such as methylene chloride or ethyl acetate. Drying and evaporation of the solvent affords the desired product. The phenyl carbamate can be synthesized by treatment of the corresponding heterocyclic amine of Formula A—NH₂ with diphenyl carbonate or phenyl chloroformate in the presence of a base such as sodium hydride, pyridine, or potassium carbonate with a catalytic amount of a catalyst, such as, 4-dimethylaminopyridine. The mixture is stirred at temperatures between 25° C. and 65° C. in a suitable solvent such as tetrahydrofuran for 12–36 hours.

The compound of Formula I can also be synthesized by the reaction of the appropriate arylsulfonylcarbamates of Formula IIIc with the heterocyclic amine IIId as shown in Equation 1b. This reaction can be carried out in the presence of various bases as described in Equation 1a, or by simply refluxing in an appropriately high boiling solvent such as dioxane. The arylsulfonylcarbamates can be synthesized by the reaction of sulfonamide II with phenyl or alkyl carbonates IIIb (or the corresponding chloroformates) in the presence of a variety of bases.

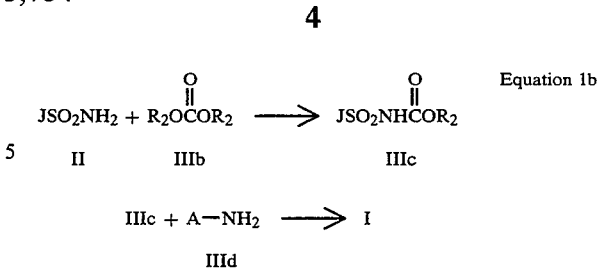

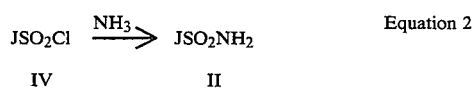

wherein

R₂ is phenyl or C₁–C₄ alkyl; and

J and A are as previously defined.

The required sulfonamide of Formula II can be synthesized by either one of the methods shown below in Equations 2 and 3.

Equation 2 depicts the reaction of the sulfonyl chloride of Formula IV with ammonia to give sulfonamide of Formula II.

$$JSO_2Cl \xrightarrow{NH_3} JSO_2NH_2$$
   IV              II

Equation 2 wherein

J is as previously defined.

The amination of Equation 2 is conveniently effected by adding at least two molar equivalents of either anhydrous ammonia or concentrated ammonium hydroxide to a solution of the sulfonyl chloride IV in a suitable solvent such as diethyl ether, tetrahydrofuran or methylene chloride at temperatures between −30° C. and 25° C. The desired sulfonamide of Formula II is isolated either by filtration, in which case the by-product ammonium chloride is removed by washing with water, or extraction into a suitable organic solvent such as methylene chloride or ethyl acetate. Drying and evaporation of the solvent then affords the product II which is usually sufficiently pure to be carried directly on to the next step.

The sulfonamide of Formula II can also be prepared as shown in Equation 3 by treatment of the corresponding N-t-butylsulfonamide VI with an excess of an acid such as trifluoroacetic (TFA), polyphosphoric (PPA), or p-toluenesulfonic acid (p-TSA).

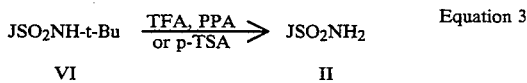

wherein

J is as previously defined.

The reaction of Equation 3 is conveniently carried out by stirring a solution of the compound of Formula VI in excess trifluoroacetic acid (approximately 0.3M) at about 25° C. for 1–72 hours. The desired sulfonamide of Formula II is then isolated by removal of the volatiles in vacuo and crystallization from a suitable solvent such as diethyl ether, 1-chlorobutane, or ethyl acetate. Alternatively, the N-t-butylsulfonamide of Formula VI can be treated with a catalytic amount of p-toluenesulfonic acid monohydrate in a solvent such as toluene or xylenes at reflux temperature for 1–6 hours. The desired product is then isolated in a manner analogous to the one described above. For use of polyphosphoric acid in the deprotection of N-t-butylsulfonamides, see J. G. Lombardino, *J. Org. Chem.*, 1971, 36, 1843–1845; for use of trifluoroacetic acid, see J. D. Catt and W. L. Matier, *J. Org. Chem.*, 1974, 39, 566–568.

The sulfonamide of Formula VI can be prepared by the reaction of the sulfonyl chloride of Formula IV with excess t-butyl amine as shown in Equation 4.

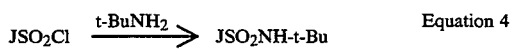

Equation 4 wherein

J is as previously defined.

The sulfonyl chloride of Formula IV can be prepared according to the procedures described in U.S. Pat. No. 4,456,469. Alternatively, the procedures of U.S. Pat. No. 4,741,764 may be utilized which described the conversion of mercapto or arylmethylthio compounds to sulfonyl chlorides via treatment with hypochlorite solution.

The sulfides of Formula V can be prepared by the reaction of a halo pyridine compound of Formula VII with an appropriate mercaptan in the presence of a base as described in U.S. Pat. No. 4,456,469 and shown in Equation 5.

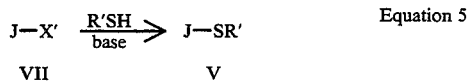

Equation 5 wherein

X' is F, Cl, or Br; and

R' is $C_1$–$C_4$ alkyl or benzyl.

A method to prepare the sulfonamide of Formula VIIIe is shown in Equation 6. The trifluoromethyl ketone intermediate VIIIa is prepared according to the procedures of Lang et al., *Helv. Chim. Acta.* 1988, 71, 596–601. In a modification of this procedure, VIIIa is then treated with ethyl malonate monoamide (or ethyl carbamoylacetate) in the presence of sodium methoxide to afford the trifluoromethyl pyridinone methyl ester VIIIb. Heating VIIIb with phosphorous oxybromide or oxalyl bromide/dimethylformamide (DMF) in methylene chloride results in the bromopyridine VIIIc. Conversion to the benzyl sulfide VIIId and the sulfonamide VIIIe is carried out as previously described.

Equation 6

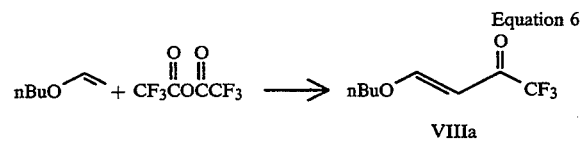

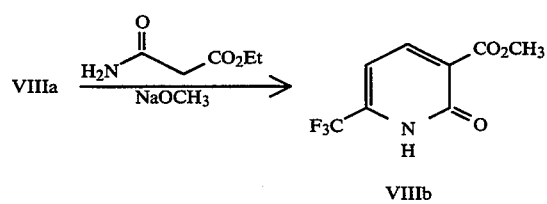

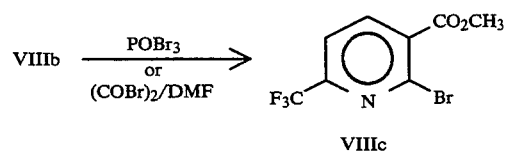

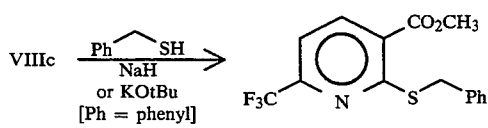

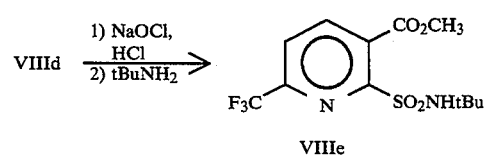

Agriculturally suitable salts of the compound of Formula I are also useful herbicides and can be prepared in a number of ways known to the art. For example, metal salts can be made by contacting the compound of Formula I with a solution of an alkali or alkaline earth metal salt having a sufficiently basic anion (e.g., hydroxide, alkoxide, carbonate or hydroxide). Quaternary amine salts can be made by similar techniques.

Salts of the compound of Formula I can also be prepared by exchange of one cation for another. For example, cationic exchange can be effected by direct contact of a solution of a salt of a compound of Formula I (e.g., alkali or quaternary amine salt) with a solution containing the cation to be exchanged. This method is most effective when the desired salt containing the exchanged cation is insoluble in the solution and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is watersoluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Temperatures are reported in degrees Celsius; abbreviations for nuclear magnetic resonance (NMR) are: S=singlet, d=doublet, t=triplet, m=multiplet, and peak positions are reported as parts per million downfield from internal tetramethylsilane. Infrared (IR) peak positions are given in reciprocal centimeters ($cm^{-1}$).

EXAMPLE 1

Preparation of methyl 1,2-dihydro-2-oxo-6-(trifluoromethyl)-3-pyridinecarboxylate (VIIIb)

To a stirred solution of 2.0 g (0.0102 mol) of 4-butoxy-1,1,1-trifluoro-3-buten-2-one (VIIIa) and 1.3 g (0.0102 mol) of ethyl malonate monoamide in 10 mL methyl alcohol was added 2.2 mL (0.0102 mol) of a 25% solution of sodium methoxide in methanol. The solution turned into a thick yellow suspension which was refluxed overnight. The suspension was cooled to room temperature, poured into water, acidified with one normal hydrochloric acid and extracted with methylene chloride. The combined organic layers were washed with brine, dried over magnesium sulfate and evaporated to afford 1.7 g (74%) of a yellow solid. m.p. 63°–64° C.; $^1$H NMR (CDCl$_3$) δ4.0 (3H, s), 7.33 (1H, d, J=8 Hz), 8.4 (1H, d, J=8 Hz); IR (mineral oil) 3080, 1675 (br), 1605, 1450, 1375 cm$^{-1}$.

EXAMPLE 2a

Preparation of methyl 2-bromo-6-(trifluoromethyl)-3-pyridinecarboxylate (VIIIc)

A suspension of 22.0 g (0.100 mol) of the product from Example 1 and 28.7 g (0.100 mol) of phosphorous oxybromide was heated at 75°–120° C. over 45 minutes utilizing an oil bath as the heat source. The reaction was also connected to a water scrubber to trap the gas by-products. The mixture was then cooled to room temperature, diluted with water and extracted with methylene chloride. The combined organic layers were washed with saturated sodium bicarbonate solution, washed with brine, dried over magnesium sulfate and evaporated to an oil which was purified by flesh chromatography utilizing 20% ethyl acetate/petroleum ether as the eluent to afford 3.8 g (13.3%) of an oil. $^1$H NMR (CDCl$_3$) δ4.0 (3H, s), 7.72 (1H, d, J=8 Hz), 8.2 (1H, d, J=8 Hz); IR (neat) 1740, 1590, 1455, 1335, 1275, 1140, 1100, 1050 cm$^{-1}$.

EXAMPLE 2b

Preparation of methyl 2-bromo-6-(trifluoromethyl)-3-pyridinecarboxylate (VIIIc)

To a stirred solution of 2.0 g (0.0091 mol) of the product from Example 1 in 25 mL methylene chloride under nitrogen was added 0.92 mL (0.0118 mol) of dimethylformamide followed by 1.57 mL (0.011 mol) of oxalyl bromide which resulted in an exotherm to 35° C. and gas evolution before all the oxalyl bromide was added. The reaction was cooled to room temperature and the remaining oxalyl bromide was added. The solution was stirred for 1 h at room temperature during which time an orange-yellow suspension appeared. The reaction was refluxed 3 h, cooled to room temperature and stirred overnight. Another 0.79 mL (0.0055 mol) of oxalyl bromide and 0.46 mL (0.006 mol) of dimethylformamide were added and refluxed 6 h and then refluxed overnight. Another 0.79 mL (0.0055 mol) of oxalyl bromide was added and refluxed 5 h. The reaction was poured into approximately 50 mL water and to this was added about 150 mL ether. The organic layer was separated, washed with brine, dried over magnesium sulfate and evaporated to an oil which was purified by flash chromatography using 20% ethyl acetate/hexanes as the eluent which afforded 1.53 g (~55%) of an oil whose NMR was similar to Example 2a, with the exception of approximately 10% contamination of dimethyloxalate.

EXAMPLE 3a

Preparation of methyl 2-[(phenylmethyl)thio]-6-(trifluoromethyl)-3-pyridinecarboxylate (VIIId)

To a stirred suspension of 0.28 g (0.008 mol) of 60% sodium hydride (in mineral oil, then washed with hexanes) in 7 mL dry dimethylformamide under nitrogen at 0° C. was added 0.8 mL (0.0067 mol) of benzyl mercaptan while maintaining the temperature below 10° C. The suspension was warmed to room temperature and stirred another 45 minutes before cooling back to 0° C. A solution of 2.0 g (0.0067 mol) of the product from Example 2a or 2b in 5 mL dry dimethylformamide was added dropwise and stirred 30 minutes at 0° C. The reaction was poured into ice water and extracted with ether. The combined organic layers were washed with brine, dried over magnesium sulfate and evaporated to afford 2.3 g (100%). $^1$H NMR (CDCl$_3$) δ, 3.94 (3H, s), 4.43 (2H, s), 7.2–7.6 (6H, m), 8.38 (1H, d, J=8Hz).

EXAMPLE 3b

Preparation of methyl 2-[(phenylmethyl)thio]-6-(trifluoromethyl)-3-pyridinecarboxylate (VIIId)

To a stirred suspension of 6.55 g (0.0584 mol) of potassium-t-butoxide in 60 mL dry dimethylformamide under nitrogen at 0° C. was added 6.84 mL (0.0584 mol) of benzyl mercaptan in 20 mL dimethylformamide while maintaining the temperature below 15° C. A solution of 15.83 g (0.053 mol) of the product from Example 2a or 2b in 20 mL dry dimethylformamide was added dropwise maintaining the temperature at 0° C. and then stirred another 30 minutes at 0° C. The reaction was poured into ice water and extracted with ether. The combined organic layers were washed with water, brine, dried over magnesium sulfate and evaporated to afford 17.84 g (100%). $^1$H NMR is similar to Example 3. IR (neat) 1725, 1675, 1575, 1135, 850 cm$^{-1}$.

EXAMPLE 4

Preparation of methyl 2-[[(1,1-dimethylethyl)amino]-sulfonyl]-6-(trifluoromethyl)-3-pyridinecarboxylate (VIIIe)

To a stirred mixture of 2.3 g (0.007 mol) of the product from Example 3a or 3b in 75 mL methylene chloride and 35 mL water cooled to 0° C. was added 2.1 mL (0.025 mol) concentrated hydrochloric acid followed by the dropwise addition of 36 mL (0.0245 mol) of a 5% sodium hypochlorite solution such that the temperature was maintained below 10° C. After the mixture was stirred another 15 minutes at 0° C., the reaction was poured into water and extracted with methylene chloride. The combined organic layers were washed with brine, dried over magnesium sulfate and filtered. The filtrate was stirred and cooled to −70° C. under nitrogen, and 2.6 g (0.035 mol) of t-butyl amine was added dropwise. The mixture was warmed to −30° C., poured into water and extracted with methylene chloride. The combined organic layers were washed with brine, dried over magnesium sulfate and evaporated. Purification by flash chromatography using 20% ethyl acetate/petroleum ether as the eluent afforded 1.07 g (45%) of a solid. m.p. 76°–83° C.; $^1$H NMR (CDCl$_3$) δ1.25 (9H, s), 4.0 (3H, s), 5.35 (NH), 7.9 (1H, m), 8.2 (1H, m); IR (mineral oil) 3320, 1745, 1335, 1140 cm$^{-1}$.

EXAMPLE 5

Preparation of methyl 2-(aminosulfonyl)-6-(trifluoromethyl)-3-pyridinecarboxylate (II)

A solution of 0.95 g (2.79 mmol) of the product from Example 4 was stirred in 40 mL trifluoroacetic acid at room temperature overnight. The solution was evaporated to an oil which was triturated with ether to afford 0.46 g (58%) of a solid. m.p. 187°–188° C. $^1$H NMR (CDCl$_3$) δ4.05 (3H, s), 5.5 (NH$_2$), 7.95 (1H, d, J=8 Hz), 8.35 (1H, d, J=8 Hz); IR (mineral oil) 3390, 3280, 1725, 1340, 1140 cm$^{-1}$.

EXAMPLE 6
Preparation of methyl 2-[[[[(4,6-dimethoxy-2-pyrimidinyl)amino]carbonyl]amino]sulfonyl]-6-(trifluoromethyl)-3-pyridinecarboxylate (I)

To a stirred solution of 0.05 g (0.176 mmol) of the product from Example 5 and 0.06 g (0.211 mmol) of phenyl (4,6-dimethoxypyrimidin-2-yl) carbamate in 0.5 mL acetonitrile was added dropwise 0.028 g (0.185 mmol) of 1,8-diazabicyclo[5.4.0]undec-7-ene and was stirred 15 minutes. The solution was diluted with water, acidified with 1 normal hydrochloric acid and extracted with methylene chloride. The combined organic layers were washed with brine, dried over magnesium sulfate and evaporated to an oil which was triturated with ether to afford 0.03 g (54%) of a solid. m.p. 130°–137° C. $^1$H NMR (CDCl$_3$) $\delta$3.96 (6H, s), 4.05 (3H, s), 5.82 (1H, s), 7.3 (NH), 7.93 (1H, d, J=approximately 8 Hz), 8.4 (1H, d, J=approximately 8 Hz), 13.1 (NH); IR (mineral oil) 3180, 1745, 1715, 1370, 1140 cm$^{-1}$.

EXAMPLE 7
Preparation of the sodium salt of methyl 2-[[[[(4,6-dimethoxy-2-pyrimidinyl)amino]carbonyl]amino]sulfonyl]-6-(trifluoromethyl)-3-pyridinecarboxylate (I)

To a stirred solution of 50.0 g (0.176 mol) methyl 2-(aminosulfonyl)-6-(trifluoromethyl)-3-pyridine-carboxylate and 55.0 g (0.200 mol) phenyl 4,6-dimethoxypyrimidine-2-yl carbamic acid ester in 75 mL dimethylformamide was added 30 mL triethylamine at room temperature. After dissolution of the solids, the amber solution was diluted with 150 mL methanol. To this solution 40 g (0.185 mol) of 25% sodium methoxide solution was slowly added at room temperature. After 10 g of the 25% sodium methoxide solution was added, the solution was seeded with 1.0 g of previously prepared title compound. The resulting precipitate was cooled to 10° C. and stirred for 30 minutes. The solid precipitate was filtered and washed with cold methanol (2×50 mL) to afford 75.7 g of a solid, m.p. 176°–177° C. dec. The solid contained 3.0% water by Karl Fisher titration and 89.2% of the title compound which was assayed by HPLC. The yield corrected for methyl 2-(aminosulfonyl)-6-(trifluoro-methyl)-3-pyridinecarboxylate and the added seed was 81.4%.

EXAMPLE 8
Preparation of the sodium salt of methyl 2-[[[[(4,6-dimethoxy-2-pyrimidinyl)amino]carbonyl]amino]sulfonyl]-6-(trifluoromethyl)-3-pyridinecarboxylate (I)

To a solution of 9.5 g (0.021 mol) methyl 2-[[[[(4,6-dimethoxy-2-pyrimidinyl)amino]carbonyl]amino]sulfonyl]-6-(trifluoromethyl)-3-pyridinecarboxylate dissolved in 40 mL methanol was added 5.0 mL (0.023 mol) of 25% sodium methoxide in methanol. The resulting slurry was stirred at room temperature for 40 min. and then filtered to afford 8.3 g of the sodium salt, m.p. 172°–173° C. dec. The water content was 5.9% by Karl Fisher titration.

By applying the procedures of U.S. Pat. No. 4,774,337 or Examples 1 through 8 and Equations 1 through 6, the compound of Formula I (Compound 1) can be prepared by one skilled in the art.

COMPOUND TABLE

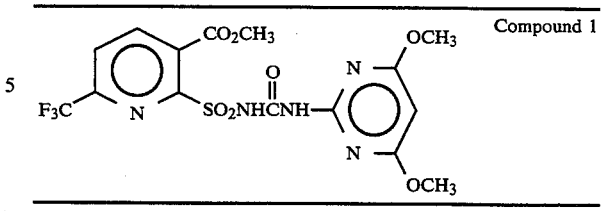

Compound 1

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 0% to 99.9% solid or liquid inert diluent(s). More specifically, they will contain these ingredients in the following approximate proportions:

|  | Weight Percent* | | |
|---|---|---|---|
|  | Active Ingredient | Diluent(s) | Surfactant(s) |
| Wettable Powders | 20–90 | 0–74 | 1–10 |
| Oil Suspension, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 1–15 |
| High Strength Compositions | 90–99 | 0–10 | 0–2 |
| Filled Film | 0.1–90 | 10–90 | 0–10 |

*Active ingredient plus at least one of a Surfactant or a Diluent equal 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff and "Perry's Chemical Engineer's Handbook", 5th Ed., McGraw-Hill, New York, 1963, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE A

High Strength Concentrate

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate | 99% |
| trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

EXAMPLE B

Wettable Powder

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE C

Aqueous Suspension

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate | 50.0% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 46.7% |

The ingredients are blended and ground together in a sand mill to produce particles essentially all under 5 microns in size.

EXAMPLE D

Oil Suspension

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE E

Oil Suspension

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE F

Aqueous Suspension

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE G

Wettable Powder

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate | 40.0% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE H

Granule

| | |
|---|---|
| wettable powder | 15% |
| gypsum | 69% |
| potassium sulfate | 16% |

The ingredients are blended in a rotating mixer and water sprayed on to accomplish granulation. When most of the material has reached the desired range of 1.0 to 0.42 mm (U.S.S. No. 18 to 40 sieves), the granules are removed, dried, and screened. Oversized material is crushed to produce additional material in the desired range. These granules contain % active ingredient.

EXAMPLE I

Wettable Powder

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate | 50% |
| sodium alkylnaphthalenesulfonate | 2% |
| low viscosity methyl cellulose | 2% |
| diatomaceous earth | 46% |

The ingredients are blended, coarsely hammer-milled and then air milled to produce particles or active ingredient essentially all below 10 microns in diameter. The product is reblended before packaging.

EXAMPLE J

Extrude Pellet

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinder about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE K

Wettable Powder

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate | 80% |
| sodium alkylnaphthalenesulfonate | 2% |
| sodium ligninsulfonate | 2% |
| synthetic amorphous silica | 3% |
| kaolinite | 13% |

The ingredients are blended and then ground in a hammermill to produce particles with an average particle size less than 25 microns in diameter. The material is reblended and sifted through a U.S.S. No. 50 sieve (0.3 mm opening) before being packaged.

EXAMPLE L

High Strength Concentrate

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate | 98.5% |
| silica aerogel | 0.5% |
| synthetic amorphous fine silica | 1.0% |

The ingredients are blended and ground in a hammermill to produce a high strength concentrate essentially all passing a U.S.S. No. 50 sieve (0.3 mm openings). This material may then be formulated in a variety of ways.

EXAMPLE M

Solution

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate sodium salt | 5% |
| water | 95% |

The salt is added directly to the water with stirring to produce the solution, which may then be packaged for use.

EXAMPLE N

Solution

| | |
|---|---|
| Methyl 2-[[[[(4,6-dimethoxy-2-pyrimidinyl)-amino]carbonyl]amino]sulfonyl]-6-(trifluoromethyl)-3-pyridinecarboxylate sodium salt | 50% |
| aqueous polyvinyl alcohol solution | 49% |
| sodium dodecylbenzene sulfonate | 1% |

The dry ingredients are ground together and then mixed into the polyvinyl alcohol solution. The blend is cast as a film of 10–40 mL on a flat surface and then dried to remove the excess water.

UTILITY

Test results indicate that the compound of the present invention is a highly active preemergent and/or postemergent herbicide or plant growth regulant. The compound has utility for pre- and/or postemergence broad-spectrum grass and broadleaf control in cereal crops. The compound is particularly useful for the control of blackgrass (*Alopecurus myosuroides*) in cereal crops such as wheat (*Triticum aestivum*), barley (*Hordeum vulgare*), oats (*Avena sativa*), rye (*Secale cereale*) and triticale (Triticum × Secale).

An effective amount of the compound of this invention is determined by a number of factors. These factors include: formulation selected, method of application, amount of vegetation present, growing conditions, etc. In general terms, an effective amount of the compound of the invention is applied at rates of from 0.001 to 20 kg/ha, with a preferred range of from 0.002 to 0.25 kg/ha. The compound of this invention may be used alone or in combination with other commercial herbicides, insecticides, or fungicides. The following list exemplifies some of the herbicides suitable for use in mixtures. A combination of the compound of this invention with one or more of the following herbicides may be particularly useful for weed control in cereal crops.

| Common Name | Chemical Name |
| --- | --- |
| amidosulfuron | N-[[[[(4,6-dimethoxy-2-pyrimidinyl)-amino]carbonyl]amino]sulfonyl]-N-methylmethanesulfonamide |
| barban | 4-chloro-2-butynyl 3-chlorocarbamate |
| bensulfuron methyl | 2-[[[[[(4,6-dimethoxy-2-pyrimidinyl)-amino]carbonyl]amino]sulfonyl]-methyl]benzoic acid, methyl ester |
| bentazon | 3-(1-methylethyl)-(1H)-2,1,3-benzo-thiadiazin-4(3H)-one, 2,2-dioxide |
| benzoylprop | N-benzoyl-N-(3,4-dichlorophenyl)-DL-alanine |
| bifenox | methyl 5-(2,4-dichlorophenoxy)-2-nitrobenzoate |
| bromoxynil | 3,5-dibromo-4-hydroxybenzonitrile |
| butachlor | N-(butoxymethyl)-2-chloro-N-(2,6-diethylphenyl)acetamide |
| chlorpropham | 1-methylethyl 3-chlorophenylcarbamate |
| chlorsulfuron | 2-chloro-N-[[[(4-methoxy-6-methyl-1,3,5-triazin-2-yl)amino]-carbonyl]benzenesulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo-[2.2.1]heptane |
| DCPA | dimethyl 2,3,5,6-tetrachloro-1,4-benzenedicarboxylate |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorophenoxy)propanoic acid |
| dichlofop | (±)-2-[4-(2,4-dichlorophenoxy)-phenoxy]propanoic acid |
| difenzoquat | 1,2-dimethyl-3,5-diphenyl-1H-pyrazolium |
| diflufenican | 2',4'-difluoro-2-(α,α,α-trifluoro-m-tolyloxy)nicotinanilide |
| DNOC | 2-methyl-4,6-dinitrophenol |
| fenoxaprop-ethyl | ethyl (±)-2-[4-[(6-chloro-2-benz-oxazolyl)oxy]phenoxy]propanoate |
| fenoxaprop-ethyl with crop safener | |
| flamprop | N-benzoyl-N-(3-chloro-4-fluoro-phenyl)-DL-alanine |
| fluazifop | (±)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)-benzenamine |
| fluorochloridine | 3-chloro-4-(chloromethyl)-1-[3-(tri-fluoromethyl)phenyl]-2-pyrrolidinone |
| fluroxypyr | 4-amino-3,5-dichloro-6-fluoro-2-pyridyloxyacetic acid |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| ioxynil | 4-hydroxy-3,5-diiodobenzonitrile |
| isoproturon | N-(4-isopropylphenyl)-N',N'-dimethylurea |
| linuron | N'-(3,4-dichlorophenyl)-N-methoxy-N-methylurea |
| MCPA | (4-chloro-2-methylphenoxy)acetic acid |
| MCPB | 4-(4-chloro-2-methylphenoxy)butanoic acid |
| mecoprop | (±)-2-(4-chloro-2-methylphenoxy)-propanoic acid |
| mefluidide | N-[2,4-dimethyl-5-[[(trifluoro-methyl)sulfonyl]amino]phenyl]-acetamide |
| methabenz-thiazuron | 1,3-dimethyl-3-(2-benzothiazolyl)-urea |
| methoxuron | N'-(3-chloro-4-methoxyphenyl)-N,N-dimethylurea |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]amino]-sulfonyl]benzoic acid, methyl ester |
| monuron | N'(4-chlorophonyl)-N,N-dimethylurea |
| neburon | 1-butyl-3-(3,4-dichlorophenyl)-1-methyl urea |
| picloram | 4-amino-3,5,6-trichloro-2-pyridine-carboxylic acid |
| PPG-1013 | 5-[2-chloro-4-(trifluoromethyl)-phenoxy]-2-nitroacetophenone oxime-O-acetic acid, methyl ester |
| propanil | N-(3,4-dichlorophenyl)propanamide |
| sulfometuron methyl | 2-[[[[(4,6-dimethyl-2-pyrimidinyl)-amino]carbonyl]amino]sulfonyl]-benzoic acid, methyl ester |
| terbuthylazine | 2-(tert-butylamino)-4-chloro-6-(ethylamino)-s-triazine |
| terbutryn | N-(1,1-dimethylethyl)-N'-ethyl-6-(methylthio)-1,3,5-triazine-2,4-dismine |
| thifensulfuron methyl | [[[[(4-methoxy-6-methyl-1,3,5-triazin-2-yl)amino]carbonyl]amino]-sulfonyl]-2-thiophenecarboxylic acid, methyl ester |
| triallate | S-(2,3,3-trichloro-2-propenyl) 3-bis(1-methylethyl)carbamothioate |
| tribenuron methyl | 2-[[[[N-(4-methoxy-6-methyl-1,3,5-triazine-2-yl)-N-methylamino]-carbonyl]amino]sulfonyl]benzoic acid, methyl ester |
| trifluralin | 2,6-dinitro-N,N-dipropyl-4-(tri-fluoromethyl)benzenamine |
| 2,4-D | (2,4-dichlorophenoxy)acetic acid |
| 2,4-DB | 4-(2,4-dichlorophenoxy)butanoic acid |

The selective herbicidal properties of the subject compound that make it useful as a cereal herbicide was discovered in a number of greenhouse and field tests. The outstanding control of blackgrass (*Alopecurus myosuroides*) by the invention compound is particularly demonstrated in results of three field tests represented by Tables D, E and F. Test descriptions and results follow.

TEST A

Seeds of barley (*Hordeum vulgare*), barnyardgrass (*Echinochloa crus-galli*), cheatgrass (*Bromus secalinus*), cocklebur (*Xanthium pensylvanicum*), corn (*Zea mays*), cotton (*Gossypium hirsutum*), crabgrass (*Digitaria* spp.), giant foxtail (*Setaria faberi*), morningglory (*Ipomoea* spp.), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately sixteen days, after which all species were compared to controls and visually evaluated. Plant response ratings, summarized in Table A, are based on a scale of 0 to 10 where 0 is no effect and 10 is complete control. A dash (-) response means no test result.

TABLE A

|              | COMPOUND 1 | |
| --- | --- | --- |
| Rate (g/ha)  | 50 | 10 |
| POSTEMERGENCE | | |
| Barley       | 6  | 2  |
| Barnyardgrass| 9  | 9  |
| Cheatgrass   | 8  | 7  |
| Cocklebur    | 10 | 10 |
| Corn         | 9  | 7  |
| Cotton       | 9  | 9  |
| Crabgrass    | 7  | 7  |
| Giant foxtail| 7  | 4  |
| Morningglory | 3  | 5  |
| Nutsedge     | —  | 10 |
| Rice         | 9  | 9  |
| Sorghum      | 7  | 2  |
| Soybean      | 9  | 9  |
| Sugar beet   | 9  | 9  |
| Velvetleaf   | 9  | 8  |
| Wheat        | 1  | 0  |
| Wild Oat     | 3  | 0  |
| POSTEMERGENCE | | |
| Barley       | 7  | 4  |
| Barnyardgrass| 9  | 5  |
| Cheatgrass   | 7  | 2  |
| Cocklebur    | 9  | —  |
| Corn         | 9  | 7  |
| Cotton       | 8  | 7  |
| Crabgrass    | 8  | 8  |
| Giant foxtail| 5  | 3  |
| Morningglory | 9  | 8  |
| Nutsedge     | 10 | 9  |
| Rice         | 10 | 9  |
| Sorghum      | 7  | 0  |
| Soybean      | 9  | 8  |
| Sugar beet   | 9  | 9  |
| Velvetleaf   | 9  | 7  |
| Wheat        | 0  | 0  |
| Wild Oat     | 3  | 0  |

TEST B

Seeds of barley (*Hordeum vulgare*), barnyardgrass (*Echinochloa crus-galli*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria* spp.), downy brome (*Bromus tectorum*), giant foxtail (*Setaria faberi*), green foxtail (*Setaria viridis*), jimsonweed (*Datura stramonium*), johnsongrass (*Sorghum halepense*), lambsquarters (*Chenopodium album*), morningglory (*Ipomoea* spp.), rape (*Brassica napus*), rice (*Oryza sativa*), sicklepod (*Cassia obtusifolia*), soybean (*Glycine max*), sugar beet (*Beta vulgaris*), teaweed (*Sida spinosa*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately 24 days, after which all species were compared to control and visually evaluated. Plant response ratings, summarized in Table B, are reported on a 0 to 10 scale where 0 is no effect and 10 is complete control. A dash (-) response means no test result.

TABLE B

|               | COMPOUND 1 | | | |
| --- | --- | --- | --- | --- |
| Rate (g/ha)   | 62 | 16 | 4  | 1  |
| POSTEMERGENCE | | | | |
| Barley        | 3  | 0  | 0  | 0  |
| Blackgrass    | 10 | 10 | 10 | 8  |
| Chickweed     | 10 | 10 | 10 | 9  |
| Cocklebur     | 10 | 10 | 10 | 10 |
| Corn          | 10 | 8  | 7  | 7  |
| Cotton        | 10 | 10 | 10 | 8  |
| Crabgrass     | 10 | 6  | 5  | 4  |
| Downy brome   | 9  | 3  | 0  | 0  |
| Giant foxtail | 6  | 3  | 0  | 0  |
| Green foxtail | 9  | 6  | 4  | 3  |
| Jimsonweed    | 10 | 10 | 10 | 10 |
| Johnsongrass  | 5  | 3  | 0  | 0  |
| Lambsquarters | 10 | 10 | 10 | 7  |
| Morningglory  | 8  | 5  | 5  | 2  |
| Nutsedge      | 10 | 10 | 10 | 5  |
| Rape          | 10 | 10 | 10 | 10 |
| Rice Dry Seed | 10 | 9  | 7  | 5  |
| Sicklepod     | 10 | 10 | 10 | 10 |
| Soybean       | 10 | 10 | 10 | 9  |
| Sugar beet    | 10 | 10 | 10 | —  |
| Teaweed       | 10 | 10 | 10 | 9  |
| Velvetleaf    | 10 | 10 | 10 | 7  |
| Wheat         | 3  | 0  | 0  | 0  |
| Wild buckwheat| 10 | 10 | 10 | 10 |
| Wild oat      | 4  | 0  | 0  | 0  |
| Barnyardgrass | 10 | 10 | 10 | 10 |
| PREEMERGENCE  | | | | |
| Barley        | 6  | 5  | 3  | 0  |
| Blackgrass    | 7  | 6  | 5  | 3  |
| Chickweed     | 8  | 7  | 7  | 5  |
| Cocklebur     | 10 | 8  | 7  | 7  |
| Corn          | 7  | 6  | 0  | 0  |
| Cotton        | 8  | 8  | 7  | 5  |
| Crabgrass     | 9  | 8  | 7  | 6  |
| Downy brome   | 5  | 3  | 0  | 0  |
| Giant foxtail | 7  | 5  | 0  | 0  |
| Green foxtail | 9  | 7  | 5  | 0  |
| Jimsonweed    | 9  | 9  | 9  | 9  |
| Johnsongrass  | 8  | 6  | 3  | 0  |
| Lambsquarters | —  | —  | —  | —  |
| Morningglory  | 8  | 6  | 3  | 0  |
| Nutsedge      | 10 | 10 | 8  | 6  |
| Rape          | 10 | 10 | 10 | 10 |
| Rice Dry Seed | 10 | 10 | 10 | 7  |
| Sicklepod     | 9  | 8  | 8  | 3  |
| Soybean       | 8  | 6  | 5  | 3  |
| Sugar beet    | 10 | 10 | 10 | 10 |
| Teaweed       | 8  | 7  | 7  | 6  |
| Velvetleaf    | 10 | 10 | 8  | 7  |
| Wheat         | 3  | 0  | 0  | 0  |
| Wild buckwheat| 10 | 10 | 9  | 9  |
| Wild oat      | 6  | 3  | 0  | 0  |

TABLE B-continued

| Rate (g/ha) | COMPOUND 1 | | | |
|---|---|---|---|---|
| | 62 | 16 | 4 | 1 |
| Barnyardgrass | 10 | 10 | 8 | 4 |

TEST C

Compounds evaluated in this test were formulated in a non-phytotoxic solvent and applied to the soil surface before plant seedlings emerged (preemergence application) and to plants that were in the one-to-four leaf stage (postemergence application). A sandy loam soil was used for the preemergence test while a mixture of sandy loan soil and greenhouse potting mix in a 60:40 ratio was used for the postemergence test. Test compounds were applied within approximately one day after planting seeds for the preemergence test. Plants of these crops and weed species were adjusted to produce plants of appropriate size for the postemergence test. All plant species were grown using normal greenhouse practices. Crop and weed species include winter barley (*Hordeum vulgare* cv. 'Igri'), bedstraw (*Galium aparine*), blackgrass (*alopecurus mysosuroides*), chickweed (*Stellaria media*), downy brome (*Bromus tectorum*), field violet (*Viola arvensis*), green foxtail (*Setaria viridis*), Persian speedwell (*Veronica persica*), rape (*Brassica napus* cv. 'Jet Neuf'), ryegrass (*Lolium multiflorum*), sugar beet (*Beta vulgaris* cv. 'US1'), sunflower (*Helianthus annuus* cv. 'Russian Giant'), spring wheat (*Triticum aestivum* cv. 'ERA'), winter wheat (*Triticum aestivum* cv. 'Talent'), wild buckwheat (*Polygonum convolvulus*), wild mustard (*Sinapis arvensis*), wild oat (*Avena fatua*), and wild radish (*Raphanus raphanistrum*). Blackgrass and wild oat were treated postemergence at two growth stages. The first stage (1) was when the plants had two to three leaves. The second stage (2) was when the plants had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table C, are based upon a 0 to 10 scale where 0 is no effect and 10 is complete control. A dash response (-) means no test result.

TABLE C

| Rate (g/ha) | COMPOUND 1 | | | | | |
|---|---|---|---|---|---|---|
| | 125 | 64 | 32 | 16 | 8 | 4 |
| POSTEMERGENCE | | | | | | |
| Blackgrass (1) | — | — | — | — | — | — |
| Blackgrass (2) | 10 | 10 | 10 | 8 | 6 | 5 |
| Chickweed | 10 | 8 | 6 | 4 | 2 | 0 |
| Downy brome | 2 | 0 | 0 | 0 | 0 | 0 |
| Field violet | 4 | 2 | 0 | 0 | 0 | 0 |
| Galium (1) | 10 | 7 | 5 | 4 | 2 | 0 |
| Green foxtail | 10 | 9 | 8 | 6 | 4 | 3 |
| Persn Speedwell | 3 | 2 | 0 | 0 | 0 | 0 |
| Rape | 10 | 10 | 10 | 10 | 10 | 10 |
| Ryegrass | 6 | 5 | 3 | 0 | 0 | 0 |
| Sugar beet | 10 | 8 | 6 | 6 | 5 | 4 |
| Sunflower | 10 | 10 | 10 | 10 | 10 | 10 |
| Wheat (Spring) | 2 | 0 | 0 | 0 | 0 | 0 |
| Wheat (Winter) | 2 | 0 | 0 | 0 | 0 | 0 |
| Wild buckwheat | 10 | 10 | 8 | 6 | 4 | 2 |
| Wild mustard | 10 | 10 | 10 | 10 | 10 | 9 |
| Wild oat (1) | 0 | 0 | 0 | 0 | 0 | 0 |
| Wild oat (2) | 0 | 0 | 0 | 0 | 0 | 0 |
| Wild radish | 10 | 10 | 10 | 10 | 10 | 10 |
| Winter Barley | 4 | 2 | 0 | 0 | 0 | 0 |
| PREEMERGENCE | | | | | | |
| Blackgrass (1) | 10 | 8 | 7 | 7 | 3 | 2 |
| Blackgrass (2) | 10 | 10 | 8 | 7 | 4 | 3 |
| Chickweed | 10 | 10 | 10 | 10 | 9 | 8 |
| Downy brome | 7 | 5 | 4 | 2 | 0 | 0 |
| Field violet | 10 | 10 | 10 | 10 | 9 | 7 |
| Galium (1) | 10 | 10 | 10 | 10 | 9 | 6 |
| Green foxtail | 10 | 8 | 7 | 6 | 4 | 2 |
| Persn Speedwell | 10 | 10 | 10 | 8 | 7 | 6 |
| Rape | 10 | 10 | 10 | 10 | 10 | 9 |
| Ryegrass | 7 | 6 | 5 | 3 | 2 | 0 |
| Sugar beet | 10 | 10 | 10 | 10 | 9 | 8 |
| Sunflower | 10 | 10 | 10 | 10 | 8 | 6 |
| Wheat (Spring) | 2 | 1 | 0 | 0 | 0 | 0 |
| Wheat (Winter) | 2 | 2 | 0 | 0 | 0 | 0 |
| Wild buckwheat | 10 | 10 | 8 | 7 | 5 | 3 |
| Wild mustard | 10 | 10 | 10 | 10 | 9 | 8 |
| Wild oat (1) | 3 | 2 | 0 | 0 | 0 | 0 |
| Wild oat (2) | 4 | 2 | 0 | 0 | 0 | 0 |
| Wild radish | 10 | 10 | 10 | 10 | 8 | 6 |
| Winter Barley | 6 | 4 | 2 | 0 | 0 | 0 |

TEST D

A field test was sown with seeds of winter wheat (*Triticum aestivum*), winter barley (*Hordeum vulgare*) and blackgrass (*Alopecurus myosuroides*) and treated postemergence with the test chemicals dissolved in a non-phytotoxic solvent. Thirty-six days after treatment the treated plants were compared to controls and visually evaluated. Plant response ratings, summarized in Table D, are based on a scale of 0 to 10 where 0 is no effect and 10 is complete control.

TABLE D

| | COMPOUND 1 (36 DAT) | | |
|---|---|---|---|
| Rate (g/ha) | Winter Wheat | Winter Barley | Blackgrass |
| 70 | 1 | 3 | 10 |
| 35 | 1 | 2 | 10 |
| 18 | 0 | 1 | 10 |
| 8 | 0 | 0 | 10 |

TEST E

A field test was sown with seeds of winter wheat (*Triticum aestivum*) and blackgrass (*Alopecurus mysuroides*) and treated postemergence with the test chemicals dissolved in a non-phytotoxic solvent. Forty-nine days after treatment the treated plants were compared to controls and visually evaluated. Plant response ratings, summarized in Table E, are based on a scale of 0 to 10 where 0 is no effect and 10 is complete control.

TABLE E

| | COMPOUND 1 (49 DAT) | |
|---|---|---|
| Rate (g/ha) | Winter Wheat | Blackgrass |
| 64 | 0 | 10 |
| 32 | 0 | 10 |
| 16 | 0 | 10 |
| 8 | 0 | 9 |

TEST F

A field test was sown with seeds of winter wheat (*Triticum aestivum*), winter barley (*Hordeum vulgare*) and blackgrass (*Alopecurus myosuroides*) and treated postemergence with the test chemicals dissolved in a non-phytotoxic solvent. Sixty-six days after treatment the treated plants were compared to controls and visually evaluated. Plant response ratings, summarized in Table F, are based on a scale of 0 to 10 where 0 is no effect and 10 is complete control.

TABLE F

COMPOUND 1 (66 DAT)

| Rate (g/ha) | Winter Wheat | Winter Barley | Blackgrass |
| --- | --- | --- | --- |
| 64 | 0 | 5 | 10 |
| 32 | 0 | 5 | 9 |
| 16 | 0 | 4 | 8 |
| 8 | 0 | 3 | 7 |
| 4 | 0 | 2 | 4 |

TEST G

Test plants of blackgrass (*Alopecurus myosuroides*), 'Talent' winter wheat (*Triticum aestivum*) and 'Igri' winter barley (*Hordeum vulgare*) were grown under greenhouse conditions to the 2 leaf stage. Standard 4" fiber pots filled with a mixture of Matapeake sandy loam soil, Sand, and Metro Mix (approximately 50:10:40 by volume) were used.

Compound 1 and the sodium salt of Compound 1 were dissolved into stock solutions using a small amount (1 ml) of acetone and water, respectively. Appropriate amounts of each stock were brought up to the normal spray volume (28 mL) in a solution of deionized water and 0.25% (wt/vol) 'X-77' surfactant. Treatments were applied to the test plants. Each formulation was tested at 2, 4, 8 and 16 g ai/ha on blackgrass, and at 8, 16, 32 and 64 g ai/ha on the cereal crops. Each treatment was replicated four times.

After treatment the test plants were returned to the greenhouse for periodic evaluation. At 21 days after treatment, blackgrass control and cereal crop injury were evaluated visually. The visual rating scale used is from 0 to 100% control, where 0 represents no visual symptoms relative to an untreated control, and 100% represents complete kill. A rating of 20% or greater on the cereal crops represents an unacceptable level of crop injury on this scale.

TABLE G

COMOUND 1 AND COMPOUND 1 SODIUM SALT FORMULATED AS TECHNICAL OR IN PVOH FILM

| Formulation Compound 1 | Rate (g ai/ha) | Weed and Crop Species* (% phytotoxicity) | | |
| --- | --- | --- | --- | --- |
| | | BKG | WWT | BWI |
| Untreated | 0 | 0** | 0 | 0 |
| PVOH Film Check | 0 | 0 | 0 | 0 |
| Compound 1 | 2 | 60 | — | — |
| (95% ai) | 4 | 74 | — | — |
| | 8 | 86 | 0 | 3 |
| | 16 | 90 | 0 | 10 |
| | 32 | — | 10 | 23 |
| | 64 | — | 25 | 38 |
| Compound 1 | 2 | 60 | — | — |
| Sodium Salt | 4 | 78 | — | — |
| (95% ai) | 8 | 88 | 0 | 3 |
| | 16 | 93 | 3 | 13 |
| | 32 | — | 8 | 23 |
| | 64 | — | 23 | 40 |
| Compound 1 | 2 | 60 | — | — |

TABLE G-continued

COMOUND 1 AND COMPOUND 1 SODIUM SALT FORMULATED AS TECHNICAL OR IN PVOH FILM

| Formulation Compound 1 | Rate (g ai/ha) | Weed and Crop Species* (% phytotoxicity) | | |
| --- | --- | --- | --- | --- |
| | | BKG | WWT | BWI |
| in PVOH | 4 | 75 | — | — |
| (approx. | 8 | 85 | 0 | 3 |
| 45% ai) | 16 | 90 | 0 | 10 |
| | 32 | — | 5 | 25 |
| | 64 | — | 20 | 38 |
| Compound 1 | 2 | 58 | — | — |
| Sodium Salt | 4 | 79 | — | — |
| in PVOH | 8 | 88 | 0 | 3 |
| (approx. | 16 | 90 | 0 | 18 |
| 45% ai) | 32 | — | 5 | 23 |
| | 64 | — | 13 | 35 |

PVOH = polyvinyl alcohol
*Weed and crop Species; BKG = blackgrass, WWT = winter wheat 'Talent' BWI = winter baley 'Igri'
**Each number represents the average of four observations

What is claimed is:

1. A compound of the formula

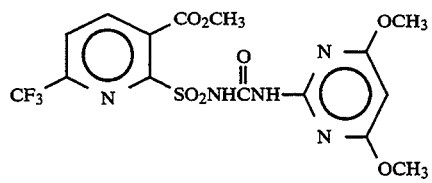

and its agriculturally suitable salts, hydrates and complexes with $C_1$-$C_4$ alcohols.

2. The compounds of claim 1 which are agriculturally suitable salts of the compound of Formula I.

3. The compounds of claim 1 wherein the salt is sodium.

4. An agriculturally suitable composition for controlling the growth of undesired vegetation comprising an effective amount of the compound of claim 1 and at least one of the following: surfactant, solid or liquid diluent.

5. An agriculturally suitable composition for controlling the growth of undesired vegetation comprising an effective amount of the compound of claim 2 and at least one of the following: surfactant, solid or liquid diluent.

6. An agriculturally suitable composition for controlling the growth of undesired vegetation comprising an effective amount of the compound of claim 3 and at least one of the following: surfactant, solid or liquid diluent.

7. A method for controlling the growth of undesired vegetation which comprises adding to the locus to be protected an effective amount of a compound of claim 1.

8. A method for controlling the growth of undesired vegetation in cereal crops which comprises adding to the locus to be protected an effective amount of a compound of claim 1.

9. A method for controlling the growth of blackgrass which comprises applying to the locus to be protected an effective amount of a compound of claim 1.

10. A method for controlling the growth of blackgrass which comprises applying to the locus to be protected an effective amount of a compound of claim 3.

* * * * *